United States Patent [19]
Stein

[11] Patent Number: 6,155,274
[45] Date of Patent: *Dec. 5, 2000

[54] FLOSS STRETCHER ARM

[76] Inventor: Peter Stein, 15/7 P. Sapir Str., Azur 58017, Israel

[ * ] Notice: This patent issued on a continued prosecution application filed under 37 CFR 1.53(d), and is subject to the twenty year patent term provisions of 35 U.S.C. 154(a)(2).

[21] Appl. No.: 09/466,373

[22] Filed: Dec. 16, 1999

[51] Int. Cl.[7] .................................................. A61C 15/00
[52] U.S. Cl. .......................................... 132/327; 132/326
[58] Field of Search .................................. 132/323, 324, 132/325, 326, 327, 328

[56] References Cited

U.S. PATENT DOCUMENTS

| | | | |
|---|---|---|---|
| 2,492,291 | 12/1949 | Johnson | 132/324 |
| 2,517,606 | 8/1950 | Streiler | 132/323 |
| 2,873,749 | 2/1959 | Gjerde | 132/323 |
| 3,882,879 | 5/1975 | Lucas | 132/325 |
| 3,998,236 | 12/1976 | Koo | 132/324 |
| 5,232,002 | 8/1993 | Mc Clallen | 132/323 |
| 5,538,023 | 7/1996 | Oczkowski et al. | 132/323 |

FOREIGN PATENT DOCUMENTS 2272161  5/1994  United Kingdom ................... 132/323

*Primary Examiner*—Todd E. Manahan

[57] ABSTRACT

A dental flossing aid device for use with a length of floss, mainly those formed as an endless loop, comprises a floss stretcher and a fork. The fork has an elongated handle and a pair of spaced apart fork prongs extending from one end of the handle. The floss stretcher comprises an elongated floss stretcher arm, a group of spaced apart floss holding teeth coupled to the stretcher arm, and a coupling pivotally connecting the fork to an end of the stretcher arm. In use, a length of floss is extended from one of the floss holding teeth and across the free ends of the prongs and the stretcher arm is pivoted so as to stretch the portion of the length of floss which extends across the substantially immobile free ends of the prongs.

29 Claims, 5 Drawing Sheets

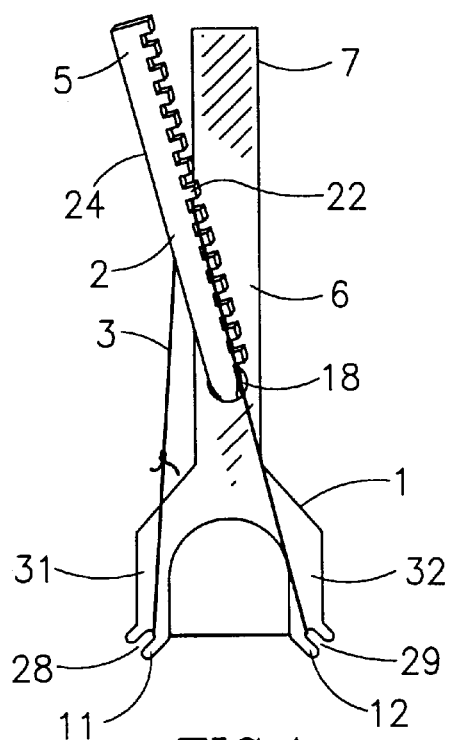
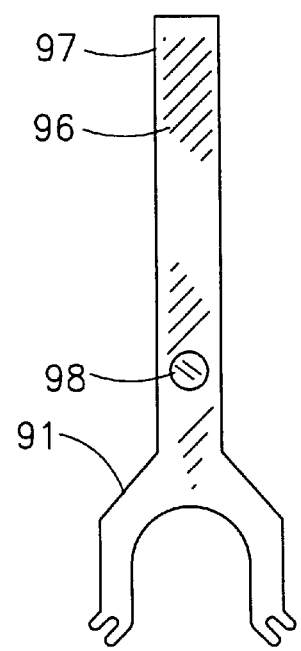
FIG.1
FIG.2
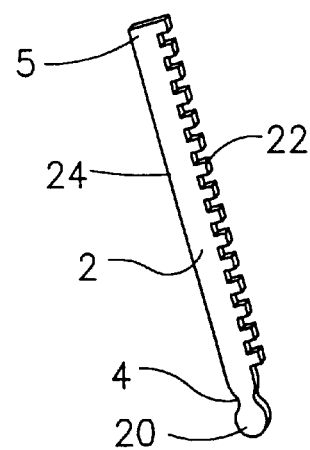
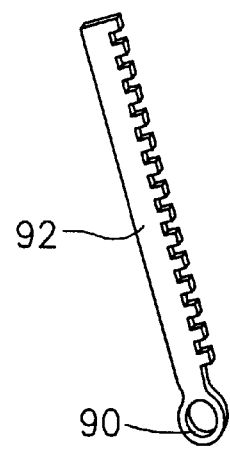
FIG.3
FIG.4

FLOSS STRETCHER ARM

BACKGROUND OF THE INVENTION

The invention relates generally to floss holders or flossless dental flosser forks which aid the use of dental floss for cleaning lateral teeth portions facing and hidden by adjacent teeth and to toothbrushes and cutlery that have dental flosser forks at the opposite end of their handle.

There are marketed two-prong dental flosser forks with attached floss advancing and tightening mechanisms and there is another type of marketed simple dental flosser fork, that has on its handle an outstanding upright pin ending in a enlarged head which allows the floss to be mounted and strained on the fork. During dental flossing the used portions of floss are getting thinner and the mounted floss is getting less strained.

Difficulties exist in prior art in that the dental flosser forks with attached floss advancing and stretching mechanisms are hard to be cleaned and kept clean, are uncomfortable when knot tying is necessary due to floss damaging during flossing, are more expensive and more demanding of their manufacturing process, while the simpler dental flosser forks don't allow the simplest manufacturing process because of pin's uprightly oriented mushroom shape and floss-squeezing contact with fork handle. And don't allow easy and fast flossing since they don't permit easy ways for at least some of the actions of floss mounting, floss removing, knot tying to fix torn apart floss during flossing, durable floss stretching, floss tightening anew, floss advancing and repositioning during flossing.

Problems remain in the prior art which are solved by the present invention.

SUMMARY OF THE INVENTION

The present invention provides floss stretcher aid arms that are easy to be manufactured alone or together with a dental-flosser fork. The stand-alone floss stretcher aid arms are easy to be mounted on dental flosser forks and to be used. When stretcher aid arms are manufactured with or mounted on dental flosser forks they allow easy floss repositioning and comfortable, easy, quick and generally immediate manual floss straining and re-stretching and loosening during flossing, therefore better cleaning of and between teeth with economical floss usage.

These and further and other objects and features of the invention are apparent in the disclosure which includes the above and ongoing description, with the claims and the drawings.

BRIEF DESCRIPTION OF THE DRAWINGS

FIG. 1 is a frontal and partially perspective view of present invention's assembly comprised of a two-prong dental flosser fork with mounted pivotal aid arm and mounted endless floss belt which are separately shown in FIGS. 5, 3 and 7 respectively.

FIG. 2 is a frontal view of a dental flosser fork including an outstanding pin topped with a larger head.

FIG. 3 is a perspective view of a flat floss strainer aid arm of the present invention that can be mounted on a fork shown in FIG. 5.

FIG. 4 is a perspective view of a flat floss strainer aid arm of the present invention that can be mounted on the uprightly outstanding pin of a fork shown in FIG. 2.

In FIG. 10 flosser fork largest face is shown in a frontal view and unhidden part of stretcher arm in a perspective view after stretcher arm is bent toward fork hidden rear face and moved in a plane that is essentially perpendicular to the plane of fork frontal and rear face.

In FIG. 11 stretcher arm is forced into a slightly bent position toward fork rear. FIG. 11 shows the flosser fork in a frontal view and stretcher arm in a perspective view.

In FIG. 18 the flosser fork and stretcher arm combination is kept by three fingers of a left hand, the stretcher arm blocked by two fingers, and a floss segment is wound multiple times on the stretcher arm near the fingers, is mounted upon the two prong ends and again is winded on the stretcher and near its free end.

DETAILED DESCRIPTION OF THE DRAWINGS

Figure 5:
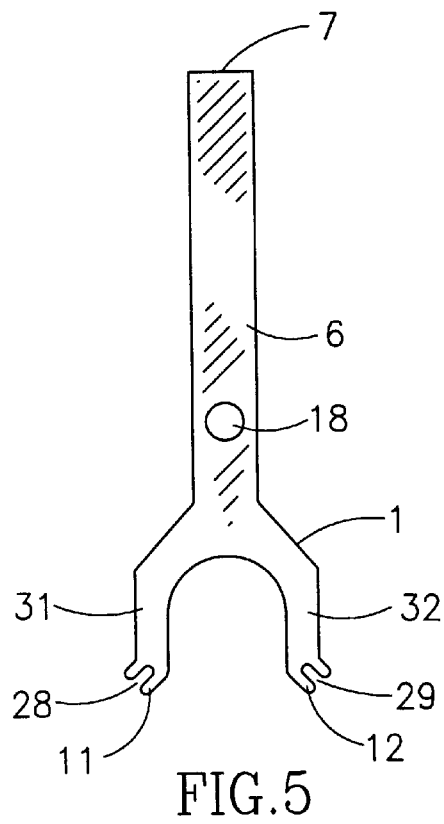
FIG. 5 is a frontal view of a dental flosser fork having an orifice allowing the connector head of a stretcher arm shown in FIG. 3 to be pushed through it.
Figure 7:
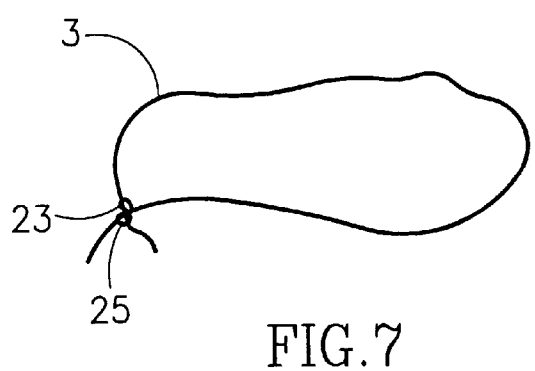
FIG. 7 is an endless floss band made from a floss shown in FIG. 16 with strongly tied knot or knots that can be mounted on a dental flosser fork.

A pivotal aid arm 2 and a dental floss band 3 are mounted on dental flosser fork 1 in the assembly shown in FIG. 1. Dental flosser fork 1 is shown in FIG. 5 and dental floss band 3 is shown in FIG. 7 and pivotal aid arm 2 is shown in FIG. 3. The assembly shown in FIG. 1 is to be grasped and held in hand with the thumb on or near aid-arm pivot holder orifice 18 and the rest of the hand around toothless edge 24 of aid arm 2 and around portion of floss 3 above and near aid arm 2, and around portion of fork handle 6 that lays between the thumb and end 7 of fork handle 6. When the assembly of FIG. 1 is grasped and held and pressured in one's band likewise a pair of tongs is grasped and used then free end 5 of aid arm 2 will be rotated around pivot holder 18 toward second end 7 of handle 6 of fork 1 and farther away from floss segment situated between prong ends 11, 12. When assembly shown in FIG. 1 is thus hand held and pressed then each portion of dental floss band 3 is constantly stretched and strained. In FIG. 1 floss 3 is situated on the rear of fork prong ends 11 and 12 and through recesses 28 and 29, and above fork handle 6, and around stretcher aid arm 2, and through a properly distanced recess of toothy edge 22 of stretcher aid arm 2 to allow a comfortable stretching.

Endless floss band 3 shown in FIG. 7 and partly shown in FIG. 1 is recommended to have a perimeter approximately equal to the double of summarized three distances: half the distance between prong ends 11 and 12, the distance from prong end 12 to pivot holder orifice 18 and the distance between pivot holder orifice 18 and middle recess of toothy edge 22 of mounted strainer aid arm 2. There could be a mark on handle 6 or on aid arm 2 shown in FIG. 1 indicating the recommended length or half length of a floss segment to be cut off and used for making floss band 3. When dental flosser fork 1 and stretcher aid arm 2 are long enough like in FIG. 1 then the length of fork 1 could be the recommended half length for a floss segment to be cut off to make endless floss band 3.

Assembly shown in FIG. 1 is to be grasped and held in one hand with the thumb on or near hidden aid arm pivot head 20 and the rest of the hand around and on portions of floss 3 and aid arm 2 and portion of fork handle 6 that lays between the thumb and forkless end 7 of fork handle 6. When aid arm 2 is pressed in a direction forming a nonzero angle with frontal and flat face of aid arm 2, then aid arm 2 could be bent. Pressing bent aid arm 2 to fork handle 6 and thus extending it or rotating bent or straight aid arm 2 toward forkless end 7 of fork handle 6 is stretching all portions of floss 3. Assembly shown in FIG. 1 can be easily grasped and pressed so that the thumb is on hidden pivot head 20 of fork 1 rear and the next finger is placed on fork 1 frontal side and on floss band 3 and close to pivot holder orifice 18 and floss portions which are situated between prong ends 11, 12, and the holding hand will lay on or close to prongs 31 and 32 thus clearing the room along prongs 31 and 32 during flossing. Assembly shown in FIG. 1 has pivot holder orifice 18 on fork handle 6 upper face so that hidden pivot head 20 of arm 2 is on fork handle 6 under face or rear.

Figure 8:
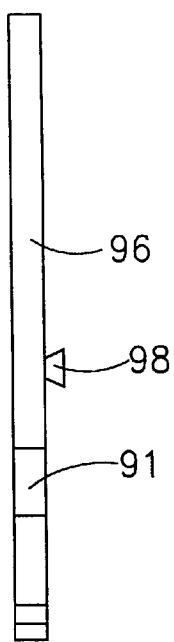
FIG. 8 is a left side view of a fork with an outstanding pin shown in FIG. 2.

Flosser fork 91 shown in FIG. 2 has an outstanding pin 98 topped with a larger head which is shown in FIG. 8 in a side view.

Diameter of pivot head 20 of stretcher arm 2 shown in FIG. 3 and diameter of the orifice 18 of flosser fork 1 shown in FIG. 5 are so that the two once assembled together they remain connected.

Flat floss strainer aid arm 92 of the present invention shown in FIG. 4 can be mounted on an outstanding pin of a fork, like the pin 98 shown on fork handle 96 in FIG. 2 and FIG. 8. The aid arm hanger 90 is ring shaped and it can be pulled over pin 98 larger head and mounted on the pin between the larger head of the pin and the fork handle. Aid arm hanger 90 could be an open hook with its opening facing the toothless edge of aid arm 92 and mountable directly on the pin neck under a larger pin head. Aid arm 92 can be somewhat flexible in directions perpendicular to its two largest faces or frontal face, and during flossing it will be positioned between the grasping and pressing palm or fingers and fork handle 96 end portion 97. When a floss band 3 is mounted on fork 91 that is assembled with stretcher arm 92 and is stretched in a grasping and pressing human hand then aid arm 92 is pressed toward fork handle 96 and floss band 3 can form a practically symmetrical shape relative to symmetry plane of fork 91 if the knot or knots are unconsidered. Stretcher aid arm 92 is flexible but it is strong enough to keep floss band 3 stretched while it is stalled between fork handle 96 and grasping and pressing hand palm or fingers. Stretcher arms 2 and 92 shown in FIGS. 3 and 4 have similar characteristics.

Fork 1 shown in frontal view in FIG. 5 has to be strong and rigid enough and it can be made of plastic or wood, for instance. Fork 1 extends from prong ends 11 and 12 to fork handle end 7 of fork handle 6. Pivot holder 18 of handle 6 is an orifice on handle 6 which is keeping stretcher arm 2 shown in FIG. 3 after its head 20 is pushed through orifice 18. Cavities 28, 29 on prongs 31 and 32 are keeping a floss on prong ends 11 and 12.

Figure 6:
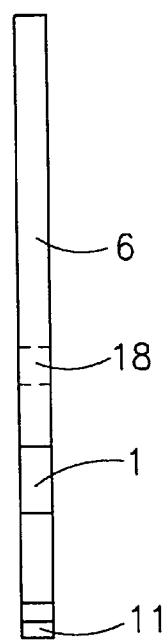
FIG. 6 is a left side view of a fork shown in FIG. 5.

FIG. 6 is a left side view of flosser fork 1 shown in FIG. 5 with fork handle 6 and prong end 11. Punctuated lines are indicating hidden empty hollow orifice 18. Flosser fork 1 can have the same thickness everywhere or thicker left and right side views than the thickness of some its interior areas, or have a shape with other varying thicknesses.

Figure 16:
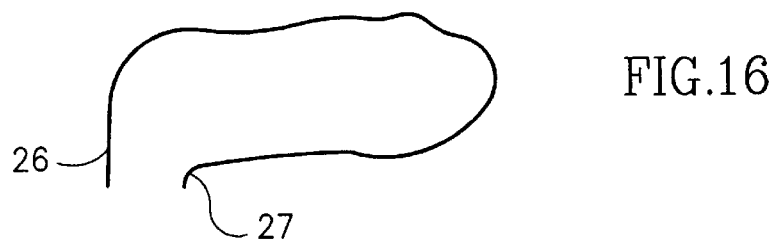
FIG. 16 is a floss which can be used to make floss belt shown in FIG. 7 by strongly tying two ends of it. If the floss shown in FIG. 16 is long enough then it can be mounted with no need for tying knots, by just creating windings around stretcher arm.

FIG. 7 shows an endless floss band 3 with tight knot 25 and made from a floss segment of proper length with ends 26 and 27 shown in FIG. 16. Endless floss band 3 shown in FIG. 7 is made and prepared to be mounted upon a flossless fork 1 and upon its coupled stretcher aid arm 2 so that an assembly shown in FIGS. 1, 11 or 12 can be obtained and which can be grasped with one hand and can be pressed together while stretching floss band 3. The movement of stretcher aid arm 2 shown in FIG. 1 could be restricted so that it would be practically always perpendicular to the imaginary straight line of the two prong tops 11 and 12, if pivot holder orifice 18 is not a round orifice but a narrow straight cut running parallel to the imaginary straight line of prong ends 11 and 12 and which is slightly shorter than a maximal diameter of hidden pivot head 20 and slightly wider than thickness of flat aid arm 2.

In FIG. 2 fork 91 is shown in frontal view having on its handle 96 an outstanding pin 98 with a larger head. End 97 of fork handle 96 could include a toothbrush, spoon or any kind of cutlery. Side view of fork 91 is shown in FIG. 8.

A diameter of head 20 of pivot portion 4 of aid arm 2 shown in FIG. 3 is larger than the diameter of the neck of pivot portion 4 and diameter of pivot holder orifice 18 of fork 1 shown in FIG. 5 is slightly shorter so that once assembled the two pieces remain connected and are twistable and rotatable one against the other around neck of pivot portion 4. Stretcher aid arm 2 shown in FIG. 3 is mounted on dental flosser fork 1 shown in FIG. 5 by lightly forcing or moving head 20 of pivot portion 4 of aid arm 2 through pivot holder orifice 18 of fork 1 shown in FIG. 5. Stretcher aid arm 2 has to be rigid enough and it can be in essence blade like which is flat and thin as shown in FIG. 3. Stretcher aid arm 2 can be made of plastic and cut off from a plastic sheet or be made by injection molding process. Stretcher aid arm 2 is in essence non-flexible and almost rigid in directions parallel to aid arm two largest faces and crossing both longer and thin edges of the blade like aid arm 2 and can be non-soft and hard enough but flexible or bendable in other directions. Stretcher aid arm 2 can have a width approximately equal to that of a portion of fork handle 6 which extends between pivot holder 18 and forkless end 7. Pivot of stretcher aid arm could be an outstanding pin or mushroom-like pin or hook at an end of stretcher aid arm. The stretcher aid arm could be made strong and rigid in every direction. Pivot holder orifice 18 has a diameter smaller than the head 20 of pivot portion 4 shown in FIG. 3 and greater than the minimal width of neck of pivot portion 4.

A diameter of head 20 of pivot portion 4 of aid arm 2 shown in FIG. 3 is larger than diameter of the neck of pivot portion 4 and diameter of pivot holder orifice 18 of fork 1 FIG. 1. Knot 25 can be strengthened with at least one adjacent or overlaying additional knot 23 as shown in FIG. 7. If aid arm 2 is much longer than the length of half perimeter of band 3 then it is recommended to start the mounting of floss band 3 shown in FIG. 7 onto a flossless assembly of fork 1 and stretcher arm 2 by first pulling floss band 3 over end 5 of assembled aid arm 2. If the perimeter of prepared endless floss band 3 is not long enough then it can be prolonged by chaining more bands together in 8-like chains.

FIG. 8 is a left side view of flosser fork 91 shown in FIG. 2 having an outstanding pin 98 and handle 96. Stretcher arm 92 can be mounted on pin 98 by pushing orifice of hanger ring 90 over the fitting or slightly larger head of pin 98.

Figure 9:
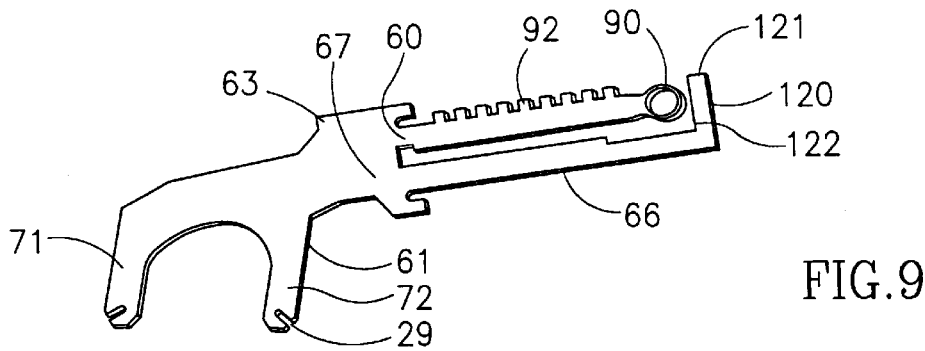
FIG. 9 is a perspective view of a one-piece combination of flosser fork and stretcher arm. The stretcher arm having a bendable connection portion connecting it to the flosser fork and a ring at its second end that can serve as a variable connector as well, as shown in FIG. 12, if fork and stretcher arm are getting separated.
Figure 10:
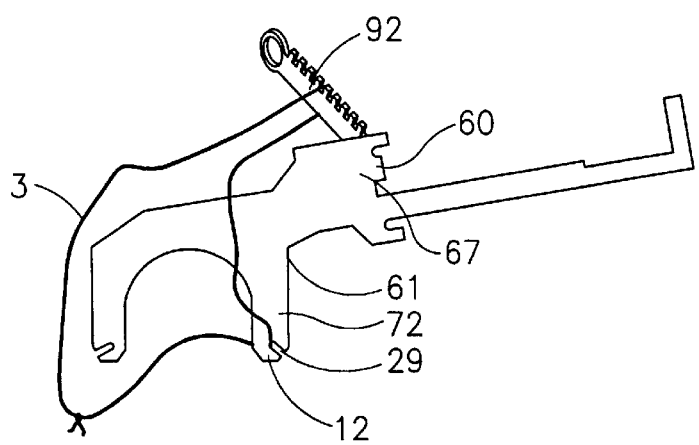
FIG. 10 is a floss band shown in FIG. 7 that is started to be mounted on a fork and stretcher arm combination shown in FIG. 9.
Figure 11:
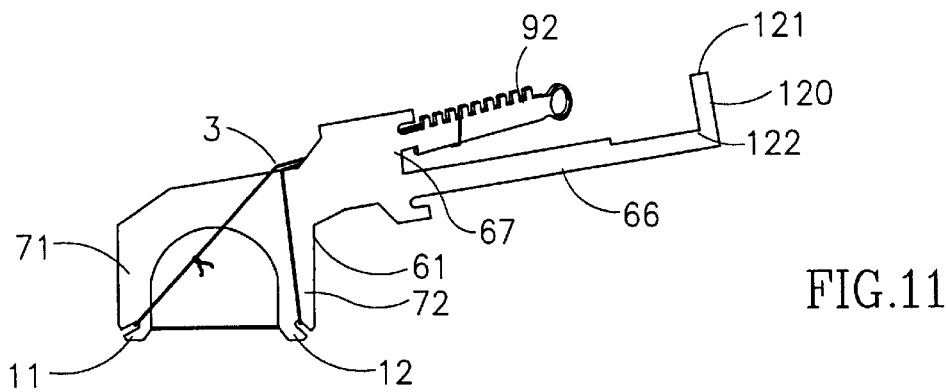
FIG. 11 is a floss belt shown in FIG. 7 and as part of FIG. 10 that is mounted and tightened on a fork and stretcher arm combination shown in FIG. 9 and FIG. 10.
Figure 12:
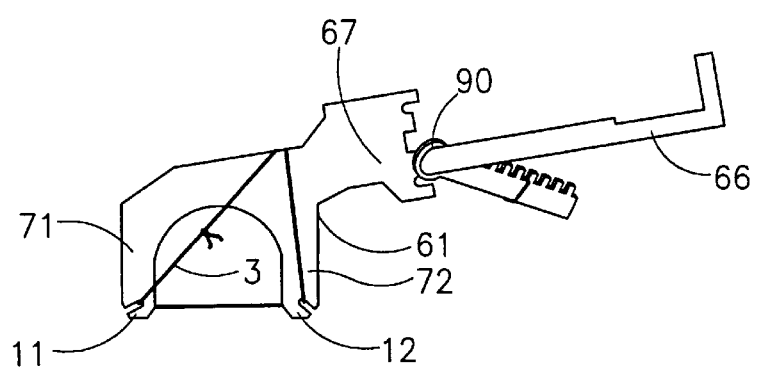
FIG. 12 is a floss belt shown in FIG. 7 that is mounted and tightened on a fork with a torn off and re-mounted stretcher and shown in FIG. 9 with stretcher arm forced into a slightly bent position and shown in a perspective view partially hidden by fork handle. Separated stretcher arm's ring end is pulled over and mounted on fork handle.
Figure 13:
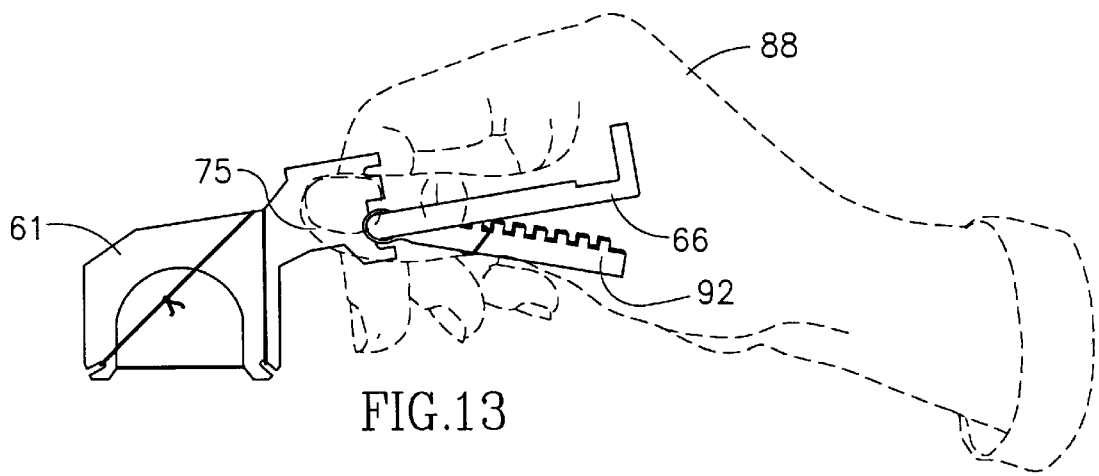
FIG. 13 is a transparent hand holding and wrapping and pressing the assembly shown in FIG. 12.
Figure 14:
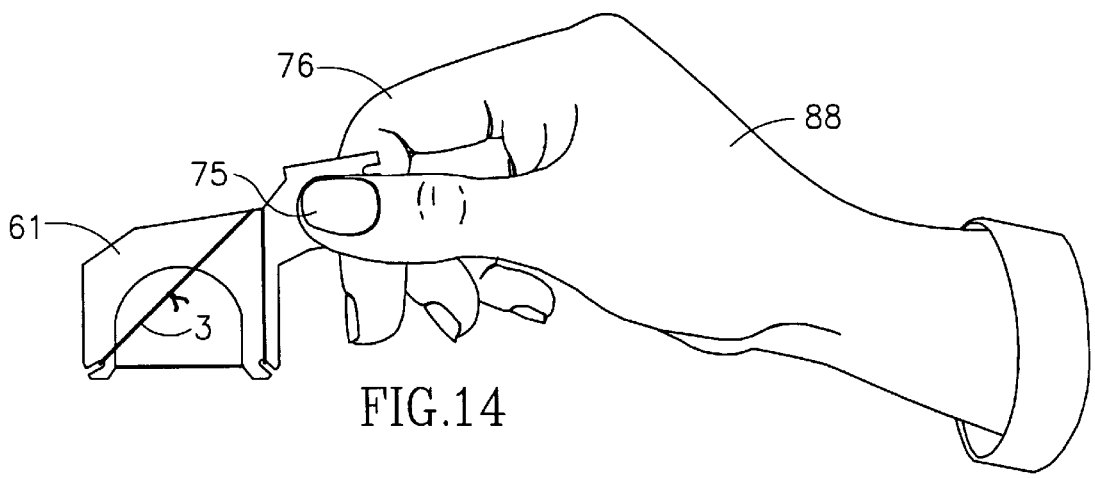
FIG. 14 is an assembly of present invention shown in FIG. 11 or 12 that is held and wrapped by and pressed in one's hand.

FIG. 9 is a perspective view of a one-piece combination 63 of flosser fork 61 and stretcher arm 92. The stretcher arm having a bendable connection portion 60 connecting it to flosser fork 61 and a ring 90 at its second end that can serve as a connector as well as shown in FIG. 12 if fork 61 and stretcher arm 92 are getting separated. Fork handle 66 is substantially tilted relative to the orientation line of prongs 71 and 72 as shown in FIGS. 9, 10 and 11 and is adjacent to a wider finger handle 67 allowing easy key-switching partial rotations of prongs 71 and 72 around an imaginary axis that is drawn through a point of handle 66 and perpendicular to prongs 71 and 72 during flossing as shown in FIGS. 13 and 14. One-piece combination 63 can have the same thickness everywhere as shown in FIG. 9 or bendable portion 60 can be thinner than the rest of combination 63 thus allowing more flexibility and easier bending.

FIG. 10 is a floss band 3 shown in FIG. 7 that is firstly mounted on stretcher arm 92 shown in FIG. 9 and then on prong end 12. Stretcher arm 92 is shown in a perspective view and fork 61 is shown in frontal view. In FIG. 10 fork 61 largest face is shown in a frontal view and stretcher arm 92 in a partially perspective view after stretcher arm is bent toward fork 61 rear and moved in a plane that is essentially perpendicular to the plane of fork 61 frontal face. In FIG. 10 stretcher arm 92 is bent at bendable portion 60 and rotated behind fork 61. Floss band 3 is placed in a recess between two teeth of arm 92 and partially behind arm 92 and through cavity 29 of prong 72 behind part of prong end 12.

FIG. 11 is a floss band 3 shown in FIG. 7 and as part of FIG. 10 that is mounted and tightened on an one-piece combination 63 of a flosser fork 61 and stretcher arm 92 shown in FIG. 9 and FIG. 10 with stretcher arm 92 forced into a slightly bent position toward fork rear and shown in a perspective view. Floss band 3 shown in FIG. 11 is placed behind prong ends 11 and 12 and in front of prongs 71 and 72 and around and behind an upper part of finger handle 67 and part of arm 92 and in front of arm 92. Mounting of floss band 3 can start by pulling it over arm 92 as described and shown in FIG. 10. Fork 61 is shown in a frontal view in FIG. 11.

FIG. 12 is a floss belt 3 shown in FIG. 7 that is mounted and tightened on fork 61 with a torn off and mounted stretcher arm 92 shown in FIG. 9 which is forced into a slightly bent position and shown in a perspective view partially hidden by and handle 66. Separated stretcher arm 92 is mounted on fork handle 66 by pulling orifice of ring 90 over handle 66 free end. Floss band 3 shown in FIG. 12 is placed behind prong ends 11 and 12 and in front of prongs 71 and 72 and behind upper part of finger handle 67 of fork 61 and part of arm 92 and in front of arm 92. Fork 61 is shown in a frontal view.

In FIG. 13 transparent band 88 shown by interrupted lines is wrapping and holding and stretching the assembly shown in FIG. 12 so that fork handle 66 and stretcher arm 92 and part of floss 3 are wrapped by palm and fingers of hand 88 and thumb 75 of hand 88 rests on ring 90 of arm 92 and on parts of finger handle 67 and fork handle 66. And on the unseen rear of fork 61 the pointing finger rests on finger handle 67 and possibly on elbow portion of stretcher arm 92 and fingers of hand 88 rest on arm 92 and part of floss 3.

In FIG. 14 hand 88 is holding and stretching the assembly shown in FIG. 12 so that fork handle 66 and stretcher arm 92 and part of floss 3 are wrapped in palm and fingers of hand 88 and thumb 75 of hand 88 rests on hidden ring 90 of arm 92 and on parts of finger handle 67 and fork handle 66, and on the rear of fork 61 pointing finger 76 rests on finger handle 67 and fingers of hand 88 rest on arm 92 and part of floss 3.

Figure 15:
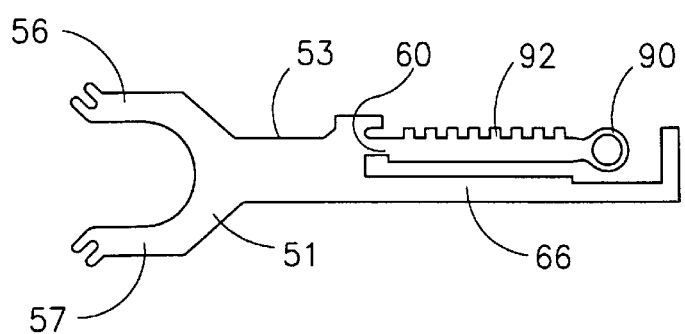
FIG. 15 is another one-piece combination of flosser fork and stretcher arm that can be used like the assembly shown in FIG. 1.

In FIG. 15 a one-piece combination 53 of fork 51 and stretcher arm 92 is shown in a frontal view. Prongs 56 and 57 and fork handle 66 are oriented along parallel lines. The way of using combination 53 with a floss is similar to that of assembly shown in FIG. 1. The usage and movement of arm 92 shown in FIG. 15 is similar to that of arm 92 shown in FIGS. 9, 10, 11 and 12.

Stretcher aid arm 92 flexibility in end portion 60 assures that it can be sufficiently tilted and bent around its end 60 and the sufficient rigidity of aid arm 92 assures that it can be used like a power arm when aid arm 92 is supported by palm or finger of pressing hand 88.

To save on expensive dental flosses or add to a short floss belt one can form a row or chain of different belts hooked together, into each other, or connected otherwise. Another way of using one short floss segment is to add to it at its two ends one or more additions of different kind of segments.

The manufacturing of fork 61 and stretcher aid arm 92 shown in FIG. 9 is very simple and it may be a plastic injection molding process. Stretcher aid arm 92 is thin and non-soft and flexible enough at its junction 60 to fork 61 while fork 61 is rigid enough. Fork handle 66 is beside aid arm 92. Aid arm 92 and fork handle 66 are close to each other. The use of flexible aid arm 92 is similar to use of a restricted aid arm 2 from the description of assembly shown in FIG. 1. During flossing with fork 61 the holding hand can be placed in such a way that the thumb will touch fork 61 near aid arm fixed end 60. Aid arm 92 can be bent sufficiently or rotated so that end 90 of aid arm 92 could remain in essence in the plane parallel to handle 66 and perpendicular to frontal face of fork 61 as in description of FIG. 10.

FIG. 16 is a floss portion with end portions 26 and 27 and can serve for making floss band 3 shown in FIG. 7. For any flosser fork proportional to either one shown in the present invention it is recommended that the length of floss between ends 26 and 27 be slightly longer than twice the largest of the two distances extending each from a fork prong end to end of fork handle, and such allowing a quick making of an endless floss belt of a proper length. The teeth on stretcher arm 92 allow the stretching of floss belts 3 of a range of lengths. Endless closed floss bands manufactured with no knots can be stretched also with present invention flosser forks and stretcher arms.

A long floss section shown in FIG. 16 extending between its two end portions may be mounted on any flosser fork of present invention by forming one or two bandages by threading the two end portions of the floss tightly around the stretcher arm and/or around the flosser handle, and thus eliminating the need of tying any knots on the floss, however it will complicate the floss advancing or re-positioning. For instance two separate bandages, wrapping portions of the stretcher arm, may easily be created on two segments of the stretcher arm of a flosser fork 61 shown in FIGS. 9, 10 and 11 by first bending and thus rotating stretcher arm 92 into an approximately perpendicular position relative to the flosser fork two faces and the handle, then keeping stretcher arm 92 in that position between two fingers of one hand and squeezing an end 26 of a long floss segment similar to the one shown in FIG. 16 between a finger of the holding hand and stretcher arm before a subsequent floss portion of the rest of the floss is winded tightly and densely multiple times around a segment of the stretcher arm 92 situated between the holding fingers and stretcher arm free end 90, preferably at least once in between two subsequent stretcher arm teeth, thus wrapping and bandaging that stretcher arm 92 portion with floss, and then moving a holding finger over the created first bandage and squeezing the other end 27 or any proper portion of the long floss segment between a holding finger and stretcher arm 92 before a subsequent floss portion situated toward firstly threaded floss bandage is winded tightly and densely multiple times around a segment of the stretcher arm 92 situated between the already created wrapping bandage and stretcher arm free end 90, thus creating a second bandage similar to the first one and an easily extendible and reducible floss arc that can be mounted on flosser fork 61 two prong ends 11 and 12, and this finishing the floss mounting operation while providing an assembly resembling the one shown in FIG. 11 with the exception that no knots are needed and the connection of floss bend and stretcher arm 92 is replaced by the two floss bandages wrapped around portions of stretcher arm 92. The two created bandages can have the same or different floss threading orientations. If the two created bandages have the same floss winding orientations then the floss portion between fork prong ends 11 and 12 can be replaced with a new one by dismounting the floss from the prongs and winding the stretched u-shaped floss arc forward a few fall circles around stretcher arm before releasing a proper length of floss from the bandage closest to stretcher arm free end 90. The second bandage might be created by threading a subsequent floss portion that is situated toward the floss second end instead of toward the floss first end, but then the floss arc advancing process will require a dismounting of the second bandage closest to arm free end 90 and before the start of the second winding the floss has to be mounted onto the two prong ends 11 and 12 and the floss slightly stretched, for the proper arc length to be assured.

Any flosser fork of present invention, including flosser fork 61, can help in tying a knot after one folds practically exactly in two a string or a floss and grabs the two meeting and overlaying ends 26 and 27 of the folded floss segment, with finger tips of thumb and a finger of one hand, and then forming a loop contour determined by the double floss line of the remaining folded floss and squeezing a closing portion of the loop above the two floss-end portions in between the floss ends keeping finger tips, so that the whole loop is kept firmly by the two finger tips, and afterward moving end 11 of the extreme prong 71 through the loop orifice from the loop-closing floss portions side and pulling the rest of the floss from the floss-end portions side of the loop to its other side through the loop orifice, and then tying a knot through a pulling motion.

A floss belt that has a perimeter too large to be simply mounted onto a given flosser fork of the present invention can be mounted on that fork so that a portion of the floss belt is threaded around the stretcher arm, however it will be difficult to advance or re-position the floss belt.

The forks and stretcher arms in the drawings have frontal view areas at least twice as big as their side view areas respectively, and their side views can have yardstick-like shapes, therefore they can be considered in essence flat or thin and similar to side views shown in FIGS. 6 and 8.

Every distance from prong end 11 to prong end 12 and every length of the prongs of present invention are so that they allow the mounted floss segment between prong ends 11 and 12 to be inserted and to touch the gum between two adjacent teeth and allow a flossing between two adjacent teeth from the gum towards tooth end and a gum stimulation.

Figure 17:
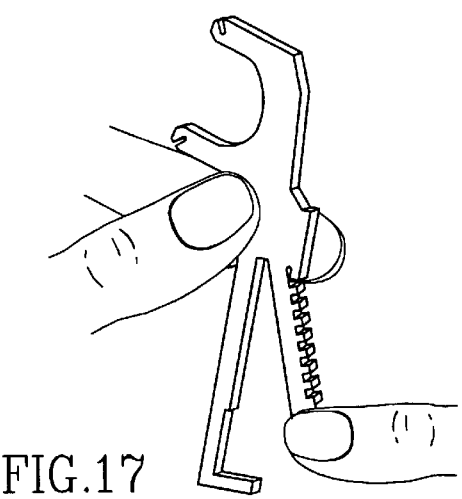
FIG. 17 is a perspective view of a flosser fork and stretcher arm combination which is kept in between two fingers of a left hand having the stretcher arm pushed and bent by a finger.
Figure 18:
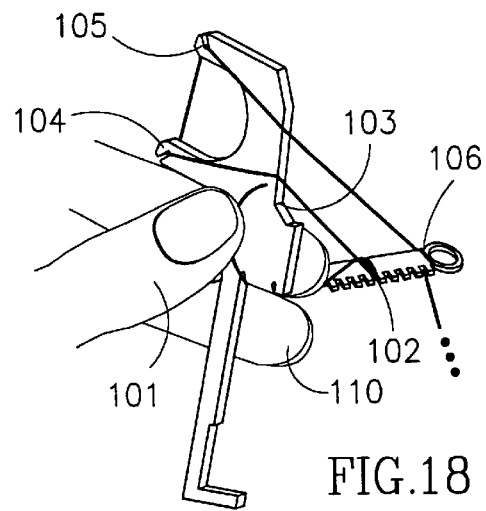
FIG. 18 is a perspective view of a flosser fork and stretcher arm combination shown in FIG. 17 having its stretcher arm bent.

FIGS. 17 and 18 illustrate a floss mounting process, by spooling or winding, described hereby through a set of instructions. Catch with left hand flosser fork 61 as shown in FIG. 17. Push backward and bend stretcher arm 92 about 90 degrees as shown in FIG. 17, then place third finger 110 as shown in FIG. 18. Then cut off about 18 inches of floss and afterward, as shown in FIG. 18, squeeze one floss end 26 under thumb 101, then wind floss about 6 times to make spool or windings 102, then guide floss above marked corner 103, then mount floss on prong ends 104 and 105, then wind floss again about 6 times while making second windings 106. Then catch with right hand the assembly made according to the steps outlined beforehand, then press stretcher arm 92 and thus strain floss, as shown in FIG. 14. Flossing between adjacent teeth can be started. To advance the floss, unwind external floss spool 106 shown partially made in FIG. 18, then dismount floss from prongs ends 104 and 105, then wind more floss around spool 102.

Figure 19:
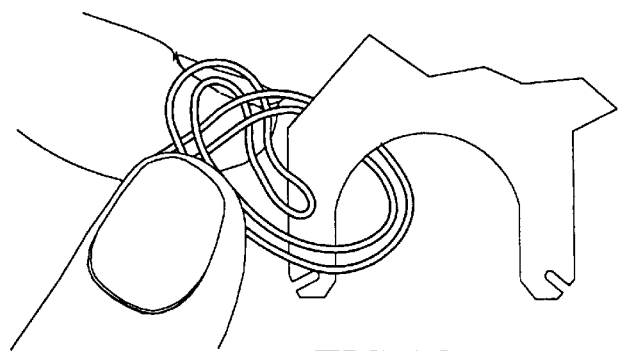
FIG. 19 is a frontal view of a floss segment folded in two and made to form a loop which is held by two fingers of a left hand and a partial frontal view of a prong and flosser fork which is scooping the middle of the floss segment or the folding point of the floss segment through the hand held loop, to tie a knot and thus form an endless floss bend or strong loop. The perspective view of the overlayed and hidden portions of the floss loop is indicated in FIG. 19 by interruptions in the floss line.

The following describes another floss mounting process, by tying knots and making an endless belt or loop 3, through a set of instructions. Cut off a floss segment of about 7.5 inches of floss, twice the length of flosser fork shown in FIGS. 9, 10, 11 and 17, and to do this first squeeze floss end 26 to handle 66 free end, then extend floss from handle 66 end to upper prong end 11, then fold floss, then cut floss near handle 66 free end. Tie knots to form a strong loop 3. A knot tying could be obtained by scooping with prong end 11 the middle of floss segment through a loop formed with the folded floss, as shown in FIG. 19. Mount loop, with no need for winding floss, as shown in FIGS. 10 and 11. Catch and glide loop 3 shown in FIGS. 10 and 11, to advance floss.

The cavities 28 and 29 and corner 103 serve as floss holding guides.

When using a floss holder shown in FIGS. 9–14 by grasping, pressing and stretching the mounted floss, the stretcher arm 92 can form an angle with handle 66 and be essentially in the plane formed by the prongs 71, 72 and the handle 66. The stretcher arm 92 shown in FIGS. 10 and 11 could be locked into a position along and below the handle 66 or rotated in the plane formed by the prong 72 and the handle 66 to divide the angle formed by the handle 66 and prong 72 into substantial angels by forcing and partially pivotally rotating it from the back face of the flosser fork 61 toward the front face of it and above the handle 66 toward the prongs while guiding the floss along the back face of finger handle 67 and above handle 66.

The set purpose of present invention is to provide cheap and easy to manufacture floss holder devices for easy and economical dental floss usage, however other different combinations of the elements presented in present invention could be found useful as well and are described hereafter.

The endless floss loop 3 could be guided partially only around a floss holding tooth of stretcher arm 2 or 92 without being guided at all around the stretcher arm 2 or 92. The floss holding teeth of stretcher arm 2 or 92 could be tilted toward the stretching direction or curved and having a partial hook like shape for a better securing of the floss around the floss holder tooth.

For consideration of simplicity the floss holding teeth are placed directly along the stretcher arm 2 and 92, however at least some of the floss holding teeth could have other carriers connected to and pulled by or rotated by the rotation of stretcher arm 2 and/or 92. Using essentially rigid questionmark, C-letter or J-letter shaped floss holders each having one of its hook shaped end serving as floss holding tooth and the other end being tied or secured to the floss holding teeth carrier, the carrier of the floss holding teeth could be a soft strong essentially non-lengthening string or tape tied at one end to a toothless or partially teethed stretcher arm at distance from the joint pivoting point of the stretcher arm and flosser fork. The floss holding teeth could be spaced apart and hung along the length of a soft carrier, or the string carrying the floss holding teeth could be replaced by a rigid carrier pivotally coupled to the toothless or partially teethed stretcher arm at distance from the pivotal joining of the stretcher arm and the flosser fork or firmly and essentially invariably secured to the toothless or partially teethed stretcher arm. For instance, a floss holding teeth carrier of a shape shown in FIG. 3 could be pivotally coupled to a stretcher arm like the one shown in FIG. 3 having an orifice between end pin 4 and end 7 similar to the orifice 18 shown in FIGS. 1, 5 and 6 distanced from the end pin 4 of the stretcher arm 2 receiving the end pin of the floss holding carrier which can be similar to pin 4 having head 20.

Each one type of stretcher arms described above could be pivotally coupled to essentially anywhere on the flosser fork, including either end of the handle 6, 96 and/or 66, and floss holder teeth could be or could not be tied or coupled to an elongated carrier joining the stretcher arm 2 and/or 92. For instance, the design of the flosser device shown in FIGS. 9, 10 and 11 could be modified so that the outstanding upper part of the finger handle 67 and the stretcher arm 92 are removed from fork 61 and separated at connection 60, then the removed parts be rotated horizontally into a mirror-image position each and thus reinstalled onto flosser fork 61 such that the removed and rotated outstanding upper part of the finger handle 67 is firmly installed or secured on the top 121 of the pin 120 at the right end of handle 66 so that its rightmost edge is in a continuation of the rightmost edge of the pin 120 and tilted leftward relative to the direction of the pin 120, while leaving the slightly tilted almost horizontal straight line drawn above the prongs to be continued by a joining and non-deviated straight line extending until an approximate left end of the upper edge of handle 66, and the removed and rotated stretcher arm end 60 is pivotally installed at or attached to or secured to the bottom 122 of the outstanding pin 120 at the rightmost end of handle 66. The handle 66 and/or stretcher arm 92 could be made relatively longer than shown in FIG. 9. In a slightly different design the floss holding teeth of the stretcher arm 92 could face the handle 66 and/or have any of the shapes presented in present invention.

An endless floss loop 3 could be mounted upon each of these modified devices in similar ways described in references to and shown in FIG. 11 except that the stretcher arm now is rotated from a position along handle 66 having end 90 near prong 72 toward a position dividing the angle formed by handle 66 and the pin 120 at the end of handle 66 to increase the distance between the floss holding teeth of the stretcher arm 92 and the handle 66 and to reduce the distance between the floss holding teeth of the stretcher arm 92 and the rightmost edge or floss holding guide at the top 121 of that pin 120, and floss loop 3 is extended from the frontal face of the prongs to behind stretcher arm 92 and that rightmost edge tilted leftward relative to the direction of the pin 120 before the folded floss turns around that floss holding guide edge and is mounted around a floss holding tooth through a recess between two subsequent floss holding teeth of the stretcher arm 92 and around the stretcher arm 92 similarly to the way shown in FIG. 11. Pressing and rotating the stretcher arm 92 back toward the handle 66 tend to reduce the angle between handle 66 and the stretcher arm 92 and stretch the floss. The floss holding teeth of the stretcher arm 92 could face the handle and/or have any of the shapes presented in present invention. The floss could be mounted only around a floss holding tooth of the stretcher arm 92 without being mounted around the stretcher arm 92, especially when the floss is in an endless floss loop 3 shape.

Some or all of the spaced apart floss holding teeth could be situated or suspended on a soft non-extendible string or a foldable or a rigid carrier coupled with the stretcher arm 2 or 92 instead of being situated directly on the stretcher arm. For instance, if the stretcher arm 92 is pivotally coupled to one of the ends of handle 66 then the pressing and rotating of the stretcher arm 92 toward paralleling and being along the handle 66 tend to reduce the angle between handle 66 and the stretcher arm 92 and are stretching the mounted length of floss shown in FIG. 16 or floss loop 3.

The stretcher arm 2 or 92 could be pivotally coupled essentially to anywhere and in many ways to the fork 1, 51, 61 or 91.

The floss could be mounted onto a flosser device described in present invention such that the floss is going at least partially around the floss holding soft or rigid carrier near a floss holding tooth and/or at least partially around the floss holding side of the floss holding tooth.

Another useful design could be obtained from FIG. 9 by forming an additional recession at the top 121 of the pin 120 at the right end of handle 66 which is a vertical mirror-image of recession 27 at the end 12 of prong 72 and removing only the stretcher arm 92 from the finger handle 67 before rotating it horizontally into a mirror-image position and pivotally coupling bendable connector 60 to the right end of handle 66 and the bottom 122 of the pin 120.

Other designs could be obtained from FIG. 9 by coupling the spaced apart floss holder teeth with the stretcher arm and/or to the teeth carrier through other means than those presented above, for instance one the upper end of each J-letter shaped floss holder or the bottom end of each question-mark shaped floss holder could be secured to an end of a distinct string secured at its other end to the stretcher arm, All the tooth keeping distinct strings could have distinct lengths and in other designs they could be secured to one and the same point of the teeth carrier or the stretcher arm. By coupling or securing only one floss holder tooth to the end of a long enough string carrying no other floss holding teeth and securing the other end of the string to the stretcher arm at a distance from its pivoting point relative to the stretcher arm, then a part of the string length could be winded as desired around the stretcher arm to fit the perimeter length of the used endless floss loop 3.

An end of an elongated and essentially rigid teeth carrier of the spaced apart floss holding teeth could be non-pivotally and firmly secured, stuck or installed to anywhere on the stretcher arm, for instance it could be at one end of the stretcher arm such that the teeth carrier is in a straight line or tilted line continuation of the stretcher arm.

Any floss holding guide could be either a recession, whole, outstanding pin on top fork or other means installed on or in the fork, and the pivotal connection of the fork to the stretcher arm has to be at distance from at least one floss holding guide of the fork such that in use a mounted endless floss loop is extended from this floss holding guide directly to a floss holding tooth.

In every design of the flosser device the direct pivotal coupling of the stretcher arm to the fork could be replaced by an indirect coupling made through a usually short length of a foldable or soft non-extendible or elongated rigid stretcher arm keeper which has at least one of its two ends pivotally secured, that is one end of the stretcher arm keeper is pivotally coupled to the fork and/or the second end of the stretcher arm keeper is pivotally coupled to one end of the stretcher arm. For instance, the short elongated connection portion 60 in FIGS. 9, 10 and 11 could be considered an elongated rigid stretcher arm keeper of the stretcher arm extending from the left side of the leftmost floss holding tooth rightward in stretcher arm 92.

The stretcher arm ends 5 and 90 could each be made in the shape of a toothpick end to serve as a toothpick as well after stretcher arms 2 and 92 are removed or stretcher arm 92 and handle 66 are properly bent away one from the other.

Figure 20:
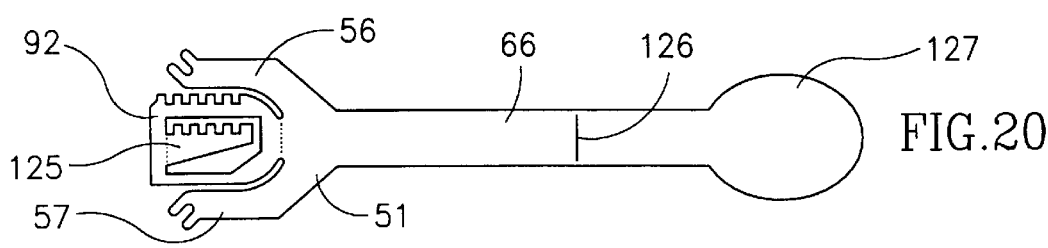
FIG. 20 is a frontal view of a one piece flosser aid having at one end of the handle two prongs, a stretcher arm and a floss holding teeth carrier, and having at the second end of the handle a spoon of a semi-spherical shape.

FIG. 20 is a frontal view of a one piece flosser aid having at one end of the handle two prongs, a stretcher arm and a floss holding teeth carrier, and having at the second end of the handle a spoon of a semi spherical shape.

Figure 21:
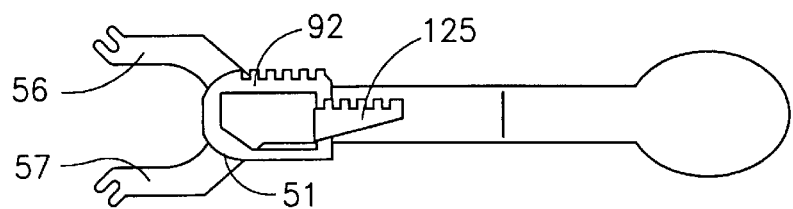
FIG. 21 is a frontal view of the one piece flosser fork and spoon combination shown in FIG. 20 having the stretcher arm and floss holding teeth carrier bent along the interrupted lines shown in FIG. 20 and in an opened and extended position along a portion of the handle.

FIG. 21 is a frontal view of the one piece flosser fork and spoon combination shown in FIG. 20 having the stretcher arm and floss holding teeth carrier bent along the interrupted lines shown in FIG. 20 and opened and extended position along a portion of the handle thus part of the stretcher arm and of the handle being hidden.

The one piece flosser fork 51 shown in FIG. 20 is having at the left end of the handle 66 two prongs 56 and 57, a stretcher arm 92, a flat floss holding teeth carrier 125 at the second end of the handle an open semi-bulb-shaped spoon 127 and mark 126 marking the recommended second end of the distance starting at one of the two free ends of prongs 56 and 57 representing the half length of floss to be cut off to make an endless floss loop 3. Stretcher arm 92 and floss holding teeth carrier 125 can be bent along the interrupted lines shown in FIG. 20 so that teeth carrier 125 is in a continuation of stretcher arm 92 as shown in FIG. 21 and serves as a stretcher arm practically extending the length of stretcher arm 92. The teeth carrier 125 could be replaced with a toothless stretcher arm to provide higher product safety and mark 126 could be placed accordingly. The flosser aid device shown in FIGS. 20 and 21 can be used in a way described earlier if a short floss loop 3 is mounted on a floss holding tooth of teeth carrier 125 and stretcher arm 92 and floss holding teeth carrier 125 are bent along the interrupted lines shown in FIG. 20 such that floss holding teeth carrier 125 is slightly bent relative to stretcher arm 92, the teeth of teeth carrier 125 have a T-letter like shape by narrowing the teeth' roots from both profile sides, teeth carrier 125 free end is pointing toward the free ends of prongs 56 and 57 and is positioned mainly above handle 66 and stretcher arm 92 bent substantially over handle 66. The use of flosser fork 51 and floss stretcher arms shown in FIG. 21 is similar to the use of the flosser fork 1 and stretcher arm 2 shown in FIG. 1, stretcher arm 92 and teeth carrier 125 shown in FIG. 21 moving in essence in a plane perpendicular to handle 66. The one piece flosser aid and spoon device shown in FIGS. 20 and 21 can be made entirely of plastic and made more flexible along the interrupted two lines shown in FIG. 20 and in essence hard elsewhere. The side view of the one piece flosser aid and spoon device shown in FIG. 20 is flat in general except the semi-circle spoon 127 portion. The teeth carrier 125 could have a toothpick-end shape.

What is claimed is:

1. A dental flossing aid for use with a length of dental floss comprising: a fork having an elongated handle, said handle having a pair of opposed ends, said fork having a pair of spaced apart prongs extending from the first of said ends of the handle, each prong having a free distal end, and an elongated floss stretcher arm having a plurality of spaced apart floss holding teeth disposed along the length thereof, said stretcher arm having a proximal end pivotally secured to said fork such that said floss stretcher arm extends substantially along and outwardly from said handle, whereby, in use, a length of dental floss is extended from at least one of said holding teeth disposed along the length of said floss stretcher arm, across the free ends of said prongs and back to said floss stretcher arm, such that grasping said handle and said floss stretcher arm pivots said floss stretcher arm thereby stretching the length of floss extending across said prongs.

2. The dental flossing aid of claim 1, wherein said fork includes a pin extending therefrom and said stretcher arm includes an aperture therein which receives said pin so as to pivotally secure said stretcher arm to said fork.

3. The dental flossing aid of claim 1, wherein said stretcher arm includes a pin extending therefrom and said fork includes an aperture therein which receives said pin so as to pivotally secure said stretcher arm to said fork.

4. The dental flossing aid of claim 1, wherein said handle, said pair of prongs and said stretcher arm are integrally formed in one piece, said stretcher arm being pivotally connected to said fork by a bendable connection portion between said proximal end of said stretcher arm and said fork.

5. The dental flossing aid of claim 1, wherein said stretcher arm has said proximal end pivotally secured to the second end of said handle.

6. The dental flossing aid of claim 5, wherein said fork includes a pin extending therefrom and said stretcher arm includes an aperture therein which receives said pin so as to pivotally secure said stretcher arm to said fork.

7. The dental flossing aid of claim 5, wherein said stretcher arm includes a pin extending therefrom and said fork includes an aperture therein which receives said pin so as to pivotally secure said stretcher arm to said fork.

8. The dental flossing aid of claim 5, wherein said handle, said pair of prongs and said stretcher arm are integrally formed in one piece, said stretcher arm being pivotally connected to said fork by a bendable connection portion between said proximal end of said stretcher arm and said fork.

9. The dental flossing aid of claim 1, wherein said stretcher arm is having said proximal end pivotally secured to said fork spaced at distance from the second end of said handle.

10. The dental flossing aid of claim 9, wherein said fork includes a pin extending therefrom and said stretcher arm includes an aperture therein which receives said pin so as to pivotally secure said stretcher arm to said fork.

11. The dental flossing aid of claim 9, wherein said stretcher arm includes a pin extending therefrom and said fork includes an aperture therein which receives said pin so as to pivotally secure said stretcher arm to said fork.

12. The dental flossing aid of claim 9, wherein said handle, said pair of prongs and said stretcher arm are integrally formed in one piece, said stretcher arm being pivotally connected to said fork by a bendable connection portion between said proximal end of said stretcher arm and said fork.

13. A dental flossing aid for use with a length of dental floss comprising:
  a fork having an elongated handle,
  said handle having a pair of opposed ends, said fork having a pair of spaced apart prongs extending from the first of said ends of the handle, each prong having a free distal end,
  said fork having at least two spaced apart floss holding guides disposed thereon,
  an elongated floss stretcher arm having a first proximal end and an opposing second end,
  a length of stretcher arm keeper having two ends, said stretcher arm keeper having one of said ends thereof secured to said fork and the second of said ends thereof secured to said first proximal end of said stretcher arm, said stretcher arm having said first proximal end thereof spaced at distance from one of said floss holding guides,
  a set of spaced apart floss holding teeth having at least one floss holding tooth,
  a length of floss holding teeth carrier having an end thereof secured to said floss stretcher arm, and
  means for connecting said set of spaced apart floss holding teeth to said length of teeth carrier,
  whereby, in use, a length of dental floss is extended from at least one of said floss holding teeth disposed along said teeth carrier, to said one of floss holding guides, across the fee ends of said prongs and back to said conjoint disposition of stretcher arm and teeth carrier and said set of floss holding teeth, such that grasping said handle and said floss stretcher arm pivots said floss stretcher arm thereby stretching the length of floss extending across said prongs.

14. The dental flossing aid of claim 13, wherein said length of stretcher arm keeper is in essence rigid and has an elongated shape, said stretcher arm keeper has at least one of said two ends thereof pivotally secured.

15. The dental flossing aid of claim 14, wherein said stretcher arm keeper has one of said ends thereof pivotally secured to said fork such that the conjoint disposition of said stretcher arm and said length of teeth carrier and said floss holding teeth and said stretcher arm keeper extends substantially paralleling and outwardly from said handle.

16. The dental flossing aid of claim 13, wherein said set of spaced apart floss holding teeth has at least two floss holding teeth, said length of floss holding teeth carrier is in essence rigid and has an elongated shape.

17. The dental flossing aid of claim 16, wherein said floss holding teeth carrier has said end thereof pivotally secured to said stretcher arm.

18. The dental flossing aid of claim 17, wherein said floss holding teeth carrier and said stretcher arm are integrally formed in one piece, said floss holding teeth carrier being pivotally connected to said stretcher arm by a bendable connection portion between said end of said floss holding teeth carrier and said stretcher arm.

19. A dental flossing aid comprising:
  a fork having an elongated handle, said handle having a pair of opposed ends, said fork having a pair of spaced apart prongs extending from the first of said ends of the handle, each prong having a free distal end,
  said fork having at least two spaced apart floss holding guides disposed thereon,
  an elongated floss stretcher arm having a first proximal end an opposing second end,
  means for connecting between said first proximal end of said stretcher arm and said fork, said stretcher arm having said first proximal end thereof pivotally connected relative to said fork and simultaneously spaced at distance from one of said floss holding guides,
  a set of spaced apart floss holding teeth having at least one floss holding tooth, and
  means for connecting said set of spaced apart floss holding teeth to said stretcher arm,
  whereby, in use, a length of dental floss is extended from at least one of said floss holding teeth, to said one of floss holding guides, across the free ends of said prongs and back to said conjoint disposition of said means for connecting said first proximal end of said stretcher arm to said fork and stretcher arm and said set of floss holding teeth and means for connecting said set of floss holding teeth to said stretcher arm, such that grasping said handle and said floss stretcher arm pivots said floss stretcher arm thereby stretching the length of floss extending across said prongs.

20. The dental flossing aid of claim 19, wherein said set of floss holding teeth has at least two floss holding teeth.

21. The dental flossing aid of claim 19, wherein said set of floss holding teethe has at least two floss holding teeth, and
  said conjoint disposition of said means for connecting said first proximal end of said stretcher arm to said fork and stretcher arm and said set of floss holding teeth and means for connecting said set of floss holding teeth to said stretcher arm extends substantially paralleling and outwardly from said handle.

22. The dental flossing aid of claim 19, wherein said means for connecting between said first proximal end of said stretcher arm and said fork is a length of stretcher arm keeper having two ends, said stretcher arm keeper having one of said ends thereof secured to said fork and the second of said ends thereof secured to said first proximal end of said stretcher arm, and said means for connecting said set of spaced apart floss holding teeth to said stretcher arm is a length of floss holding teeth carrier secured to said floss stretcher arm and means for connecting said set of spaced apart floss holding teeth to said teeth carrier.

23. The dental flossing aid of claim 22, wherein said length of stretcher arm keeper is in essence rigid and has an elongated shape, said stretcher arm keeper has at least one of said ends thereof pivotally secured such that the conjoint disposition of stretcher arm and teeth carrier and said length of floss holding teeth carrier and said set of floss holding teeth and means for connecting said set of floss holding teeth to said length of teeth carrier extends substantially paralleling and outwardly from said handle.

24. The dental flossing aid of claim 22, wherein said floss holding teeth carrier and said stretcher arm are integrally formed in one piece.

25. The dental flossing aid of claim 19, wherein said means for connecting between said first proximal end of said stretcher arm and said fork arm is a length of stretcher arm keeper having two ends, said stretcher arm keeper having one of said ends thereof secured to said fork and the second of said ends thereof secured to said first proximal end of said stretcher arm.

26. The dental flossing aid of claim 25, wherein said set of spaced apart floss holding teeth has at least two floss holding teeth.

27. The dental flossing aid of claim 26, wherein said length of floss holding teeth carrier is in essence rigid and has an elongated shape.

28. The dental flossing aid of claim 26, wherein said length of floss holding teeth carrier is in essence rigid and has an elongated shape, and teeth carrier has an end thereof pivotally secured to said stretcher arm, said floss holding teeth carrier and said stretcher arm are integrally formed in one piece.

29. The dental flossing aid of claim 19, wherein said stretcher arm has said first proximal end thereof pivotally secured to said fork, and said means for connecting said set of spaced apart floss holding teeth to said stretcher arm is a length of floss holding teeth carrier secured to said floss stretcher arm and means for connecting said set of spaced apart floss holding teeth to said teeth carrier.

* * * * *

UNITED STATES PATENT AND TRADEMARK OFFICE
CERTIFICATE OF CORRECTION

PATENT NO. : 6,155,274
DATED : December 5, 2000
INVENTOR(S) : Peter Stein

Page 1 of 1

It is certified that error appears in the above-identified patent and that said Letters Patent is hereby corrected as shown below:

Please insert in the title page, and additionally please insert in Column 1, line 2,
-- Continuation-in-part of Ser. No. 09/137,646, Aug. 20, 1998, abandoned. --

Signed and Sealed this

Eleventh Day of December, 2001

*Attest:*

*Nicholas P. Godici*

*Attesting Officer*

NICHOLAS P. GODICI
*Acting Director of the United States Patent and Trademark Office*